(12) United States Patent
Liu (10) Patent No.: US 11,246,568 B2
(45) Date of Patent: Feb. 15, 2022

(54) 3D ULTRASOUND IMAGING SYSTEM

(71) Applicant: Ying Liu, Hong Kong (HK)

(72) Inventor: Ying Liu, Hong Kong (HK)

(73) Assignee: SHENZHEN DANSHA TECHNOLOGY CO., LTD., Guangdong (CN)

( * ) Notice: Subject to any disclaimer, the term of this patent is extended or adjusted under 35 U.S.C. 154(b) by 475 days.

(21) Appl. No.: 16/393,976

(22) Filed: Apr. 25, 2019

(65) Prior Publication Data
US 2019/0247020 A1    Aug. 15, 2019

(51) Int. Cl.
| | |
|---|---|
| B06B 1/06 | (2006.01) |
| H01L 41/04 | (2006.01) |
| A61B 8/00 | (2006.01) |
| A61B 8/14 | (2006.01) |
| B06B 1/02 | (2006.01) |
| B06B 3/00 | (2006.01) |
| G10K 11/34 | (2006.01) |
| G01S 15/89 | (2006.01) |
| H01H 89/00 | (2006.01) |
| H01G 2/00 | (2006.01) |
| H01G 9/28 | (2006.01) |
| H01L 41/113 | (2006.01) |

(52) U.S. Cl.
CPC ........... *A61B 8/4494* (2013.01); *A61B 8/145* (2013.01); *A61B 8/54* (2013.01); *B06B 1/0207* (2013.01); *B06B 1/06* (2013.01); *B06B 3/00* (2013.01); *G01S 15/8993* (2013.01); *G10K 11/341* (2013.01); *H01G 2/00* (2013.01); *H01G 9/28* (2013.01); *H01H 89/00* (2013.01); *H01L 41/042* (2013.01); *B06B 2201/76* (2013.01); *H01L 41/1132* (2013.01)

(58) Field of Classification Search
CPC ....... B06B 1/06; B06B 1/0607; B06B 1/0622; H01L 41/1132; H01L 41/042
USPC ......................................... 310/322, 334, 335
See application file for complete search history.

(56) References Cited

U.S. PATENT DOCUMENTS

| | | |
|---|---|---|
| 2015/0374335 A1 | 12/2015 | Brown et al. |
| 2017/0310320 A1 | 10/2017 | Bottarel et al. |
| 2018/0069169 A1* | 3/2018 | Ota .......................... H01L 41/22 |

FOREIGN PATENT DOCUMENTS

| | | |
|---|---|---|
| GB | 2511556 A | 9/2014 |
| WO | 03/000137 A1 | 1/2003 |

* cited by examiner

*Primary Examiner* — Derek J Rosenau (57) ABSTRACT

A circuit for 3D ultrasound imaging systems includes multiple sensor units, multiple unit circuits and multiple row sharing circuits. The unit circuits are connected with the sensor units respectively. Each row of unit circuits share a row sharing circuit. Each unit circuit includes a first electrically controlled switch, a second electrically controlled switch and a control circuit. Each row sharing circuit includes a signal transmission bus, a signal receiving bus and a row main control circuit. The signal transmission bus and the signal receiving bus of each row sharing circuit extend through a corresponding row of unit circuits. The row main control circuit of each row is configured to transmit main control signals, transmission control signals and receiving control signals to a corresponding row of unit circuits so as to select the corresponding sensor units to transmit or receive ultrasound signals.

20 Claims, 8 Drawing Sheets

3D ULTRASOUND IMAGING SYSTEM

FIELD OF THE PATENT APPLICATION

The present patent application generally relates to medical electronics and more specifically to a 3D ultrasound imaging system.

BACKGROUND

A complete blood cell count is an important index of a blood test. Vascular imaging, especially cardiovascular imaging, is often desired to illustrate as much as possible the shape, composition, physical characteristics and other aspects of the atheromatous plaque in vessels since this information is helpful for early diagnosis and interventional therapy of vascular diseases. 2D ultrasound imaging systems are widely applied in the above-mentioned diagnosis, but only images of a single location or images of a single plane can be obtained with such means. In addition, since the complex condition of 3D structures cannot be reflected in real time, the real condition of vessels is often misjudged and therefore further diagnosis and treatment is interfered or misled. Other means such as a computed tomography (CT) examination is harmful to the human body and a nuclear magnetic resonance imaging (MRI) examination is relatively high in cost. Therefore, 3D ultrasound imaging systems with low examination costs and harmlessness to the human body draw more and more attention of the public.

A 3D ultrasound imaging system can provide 3D images in real time and realize accurate detection of indexes such as the flow rate of blood in vessels, the development of atheromatous plaques and other indexes. However, realizing 3D ultrasound imaging often requires a large number of ultrasound sensors and therefore leads to a large number of data channels and poses a challenge to the realization of large-scale integration of sensor modules and the design of signal transceiver circuits. On the other hand, the practical requirements of 3D ultrasound imaging for medical detection require that the usage position and direction of ultrasound sensors should have stronger reconfigurability and should be fast switchable from multiple specific and complex configuration schemes. A conventional 3D ultrasound imaging system only provides several optional and less complex schemes in this aspect and therefore restricts the application of the 3D ultrasound imaging system.

SUMMARY

The present patent application is directed to a 3D ultrasound imaging system. In one aspect, the 3D ultrasound imaging system includes multiple sensor units, multiple unit circuits corresponding to the multiple sensor units and connected with the multiple sensor units respectively, and multiple row sharing circuits. Each unit circuit includes a first electrically controlled switch, a second electrically controlled switch and a control circuit. Each row sharing circuit includes a signal transmission bus, a signal receiving bus and a row main control circuit. Each row of unit circuits share a row sharing circuit. The signal transmission bus and the signal receiving bus of each row sharing circuit extend through a corresponding row of unit circuits. The row main control circuit of each row is configured to transmit main control signals, transmission control signals and receiving control signals to a corresponding row of unit circuits so as to select the corresponding sensor units to transmit or receive ultrasound signals. The first electrically controlled switch is configured to control whether the corresponding sensor unit participates transmission of ultrasound signals. The second electrically controlled switch is configured to control whether the corresponding sensor unit participates receiving of ultrasound signals. The control circuit is a programmable logic control circuit configured to control switching of the first electrically controlled switch and the second electrically controlled switch. The first electrically controlled switch includes a first electronic switch and a second electronic switch. The second electrically controlled switch includes a third electronic switch and a fourth electronic switch. The control circuit includes a first main control electronic switch, a second main control electronic switch, an AND gate chip, a diode, a capacitor, a first inverter and a second inverter. The first electronic switch, the second electronic switch, the third electronic switch, the fourth electronic switch, the first main control electronic switch and the second main control electronic switch are N-type Metal-Oxide Semiconductor Field Effect Transistors, each including a gate electrode, a drain electrode and a source electrode. The drain electrode of the first electronic switch is connected with a corresponding sensor unit, the source electrode of the first electronic switch is connected with the drain electrode of the second electronic switch and the gate electrode of the first electronic switch is connected with the gate electrode of the second electronic switch. The source electrode of the second electronic switch is connected with the signal transmission bus. The source electrode of the first main control electronic switch is connected with the gate electrode of the first electronic switch, the drain electrode of the first main control electronic switch receives the transmission control signal and the gate electrode of the first main control electronic switch is connected with a reference voltage through the diode. The gate electrode of the first main control electronic switch is connected with the output port of the AND gate chip through the capacitor. A first input port of the AND gate chip receives the main control signal and a second input port of the AND gate chip receives the transmission control signal. The source electrode of the third electronic switch is connected with the corresponding sensor unit, the drain electrode of the third electronic switch is connected with the source electrode of the fourth electronic switch and the gate electrode of the third electronic switch receives the transmission control signal through the first inverter. The gate electrode of the fourth electronic switch receives the receiving control signal and the drain electrode of the fourth electronic switch is connected with the signal receiving bus. The drain electrode of the second main control electronic switch is connected with the signal receiving bus, the source electrode of the second main control electronic switch is connected to the ground and the gate electrode of the second main control electronic switch receives the receiving control signal through the second inverter.

The 3D ultrasound imaging system may further include a circuit board; multiple transceiver chips; and multiple sensor modules. The multiple transceiver chips may be integrated on the circuit board and jointed sequentially, and thus forming a matrix structure. The multiple sensor modules may be jointed sequentially and thus forming a matrix structure and individually corresponding to the multiple transceiver chips. Each sensor module may be integrated on a corresponding transceiver chip respectively. Each sensor module may include the multiple sensor units in an arrangement of a matrix. Each transceiver chip may include the multiple unit circuits in an arrangement of a matrix. At least one transceiver chip of each row of transceiver chips may include the multiple row sharing circuits.

In another aspect, the present patent application provides a 3D ultrasound imaging system. The 3D ultrasound imaging system includes a circuit board, multiple transceiver chips and multiple sensor modules. The multiple transceiver chips are integrated on the circuit board. The multiple sensor modules are individually corresponding to the multiple transceiver chips. Each sensor module is integrated on a corresponding transceiver chip respectively. Each sensor module includes multiple sensor units. Each transceiver chip includes multiple unit circuits. The multiple unit circuits are individually corresponding to the multiple sensor units and connected with the multiple sensor units respectively. At least one transceiver chip of each row of transceiver chips includes multiple row sharing circuits. Each row of unit circuits share a row sharing circuit. The row sharing circuit includes a signal transmission bus, a signal receiving bus and a row main control circuit. The signal transmission bus and the signal receiving bus of each row sharing circuit extend through a corresponding row of unit circuits. The row main control circuit of each row is configured to transmit main control signals, transmission control signals and receiving control signals to a corresponding row of unit circuits so as to select the corresponding sensor units to transmit or receive ultrasound signals. Each unit circuit includes a first electrically controlled switch, a second electrically controlled switch and a control circuit. The first electrically controlled switch is configured to control whether the corresponding sensor unit participates transmission of ultrasound signals. The second electrically controlled switch is configured to control whether the corresponding sensor unit participates receiving of ultrasound signals. The control circuit is configured to control switching of the first electrically controlled switch and the second electrically controlled switch. The first electrically controlled switch includes a first electronic switch and a second electronic switch. The second electrically controlled switch includes a third electronic switch and a fourth electronic switch. The control circuit includes a first main control electronic switch, a second main control electronic switch, an AND gate chip, a diode, a capacitor, a first inverter and a second inverter. The first electronic switch, the second electronic switch, the third electronic switch, the fourth electronic switch, the first main control electronic switch and the second main control electronic switch are N-type Metal-Oxide Semiconductor Field Effect Transistors, each including a gate electrode, a drain electrode and a source electrode. The drain electrode of the first electronic switch is connected with the corresponding sensor unit, the source electrode of the first electronic switch is connected with the drain electrode of the second electronic switch and the gate electrode of the first electronic switch is connected with the gate electrode of the second electronic switch. The source electrode of the second electronic switch is connected with the signal transmission bus. The source electrode of the first main control electronic switch is connected with the gate electrode of the first electronic switch, the drain electrode of the first main control electronic switch receives the transmission control signal and the gate electrode of the first main control electronic switch is connected with a reference voltage through the diode. The gate electrode of the first main control electronic switch is connected with the output port of the AND gate chip through the capacitor. A first input port of the AND gate chip receives the main control signal and a second input port receives the transmission control signal. The source electrode of the third electronic switch is connected with the corresponding sensor unit, the drain electrode of the third electronic switch is connected with the source electrode of the fourth electronic switch and the gate electrode of the third electronic switch receives the transmission control signal through the first inverter. The gate electrode of the fourth electronic switch receives the receiving control signal and the drain electrode of the fourth electronic switch is connected with the signal receiving bus. The drain electrode of the second main control electronic switch is connected with the signal receiving bus, the source electrode of the second main control electronic switch is connected to the ground and the gate electrode of the second main control electronic switch receives the receiving control signal through the second inverter.

The multiple transceiver chips may be jointed sequentially and thus forming a matrix structure. The multiple sensor modules may be jointed sequentially and thus forming a matrix structure.

Each transceiver chip in a row of transceiver chips may include the multiple row sharing circuits and each row sharing circuit may only transmit main control signals, transmission control signals and receiving control signals to the corresponding row of unit circuits in the transceiver chip.

Only one transceiver chip in a row of transceiver chips may include the multiple row sharing circuits and each row sharing circuit may transmit main control signals, transmission control signals and receiving control signals to the corresponding row of unit circuits in all transceiver chips.

Each row sharing circuit may further include a driver circuit and a low-noise amplifier which are sitting on the signal receiving bus. The driver circuit may be connected with the multiple unit circuits through the low-noise amplifier. The low-noise amplifier may be configured to amplify signals on the signal receiving bus. The driver circuit may be configured to further amplify the output of the low-noise amplifier and transmit the signals amplified by the driver circuit to the row main control circuit.

The multiple row sharing circuits may operate sequentially. After the row sharing circuit of the first row may select a target sensor unit from the corresponding row of sensor units, the row sharing circuit of the second row may begin to select a target sensor unit from the corresponding row of sensor units. The process may go on until all row sharing circuits may finish selecting the target sensor units for the corresponding rows.

The multiple row sharing circuits may operate simultaneously and may select sensor units in a predetermined column from the sensor units in all corresponding rows as the target sensor units.

The multiple row sharing circuits may operate simultaneously and each row sharing circuit may first select a sensor unit from the corresponding row of sensor units as a preset sensor unit. Then the multiple row sharing circuits may operate simultaneously and each row sharing circuit may select a sensor unit adjacent to the preset sensor unit by one or multiple columns from the corresponding row of sensor units as the target sensor unit.

In yet another aspect, the present patent application provides a 3D ultrasound imaging system. The 3D ultrasound imaging system includes multiple sensor units, multiple unit circuits corresponding to the multiple sensor units and connected with the multiple sensor units respectively, and multiple row sharing circuits. Each unit circuit includes a first electrically controlled switch, a second electrically controlled switch and a control circuit. Each row sharing circuit includes a signal transmission bus, a signal receiving bus and a row main control circuit. Each row of unit circuits share a row sharing circuit. The signal transmission bus and the signal receiving bus of each row sharing circuit extend through a corresponding row of unit circuits. The row main control circuit of each row is configured to transmit main control signals, transmission control signals and receiving control signals to a corresponding row of unit circuits so as to select the corresponding sensor units to transmit or receive ultrasound signals. The first electrically controlled switch is configured to control whether the corresponding sensor unit participates transmission of ultrasound signals. The second electrically controlled switch is configured to control whether the corresponding sensor unit participates receiving of ultrasound signals. The control circuit is a programmable logic control circuit configured to control switching of the first electrically controlled switch and the second electrically controlled switch. The first electrically controlled switch includes a first electronic switch and a second electronic switch. The second electrically controlled switch includes a third electronic switch and a fourth electronic switch. The control circuit includes a first main control electronic switch, a second main control electronic switch, an AND gate chip, a diode, a capacitor, a first inverter and a second inverter.

The first electronic switch, the second electronic switch, the third electronic switch, the fourth electronic switch, the first main control electronic switch and the second main control electronic switch may be N-type Metal-Oxide Semiconductor Field Effect Transistors, each may be including a gate electrode, a drain electrode and a source electrode.

The drain electrode of the first electronic switch may be connected with a corresponding sensor unit, the source electrode of the first electronic switch may be connected with the drain electrode of the second electronic switch and the gate electrode of the first electronic switch may be connected with the gate electrode of the second electronic switch.

The source electrode of the second electronic switch may be connected with the signal transmission bus. The source electrode of the first main control electronic switch may be connected with the gate electrode of the first electronic switch, the drain electrode of the first main control electronic switch may receive the transmission control signal and the gate electrode of the first main control electronic switch may be connected with a reference voltage through the diode.

The gate electrode of the first main control electronic switch may be connected with the output port of the AND gate chip through the capacitor. A first input port of the AND gate chip may receive the main control signal and a second input port of the AND gate chip may receive the transmission control signal.

The source electrode of the third electronic switch may be connected with the corresponding sensor unit, the drain electrode of the third electronic switch may be connected with the source electrode of the fourth electronic switch and the gate electrode of the third electronic switch may receive the transmission control signal through the first inverter. The gate electrode of the fourth electronic switch may receive the receiving control signal and the drain electrode of the fourth electronic switch may be connected with the signal receiving bus. The drain electrode of the second main control electronic switch may be connected with the signal receiving bus, the source electrode of the second main control electronic switch may be connected to the ground and the gate electrode of the second main control electronic switch may receive the receiving control signal through the second inverter.

The 3D ultrasound imaging system may further include a circuit board; multiple transceiver chips; and multiple sensor modules.

The multiple transceiver chips may be integrated on the circuit board and jointed sequentially, and thus forming a matrix structure. The multiple sensor modules may be jointed sequentially and thus forming a matrix structure and individually corresponding to the multiple transceiver chips.

Each sensor module may be integrated on a corresponding transceiver chip respectively. Each sensor module may include the multiple sensor units in an arrangement of a matrix. Each transceiver chip may include the multiple unit circuits in an arrangement of a matrix. At least one transceiver chip of each row of transceiver chips may include the multiple row sharing circuits.

DETAILED DESCRIPTION

Reference will now be made in detail to a preferred embodiment of the 3D ultrasound imaging system disclosed in the present patent application, examples of which are also provided in the following description. Exemplary embodiments of the 3D ultrasound imaging system disclosed in the present patent application are described in detail, although it will be apparent to those skilled in the relevant art that some features that are not particularly important to an understanding of the 3D ultrasound imaging system may not be shown for the sake of clarity.

Furthermore, it should be understood that the 3D ultrasound imaging system disclosed in the present patent application is not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure.

Figure 1:
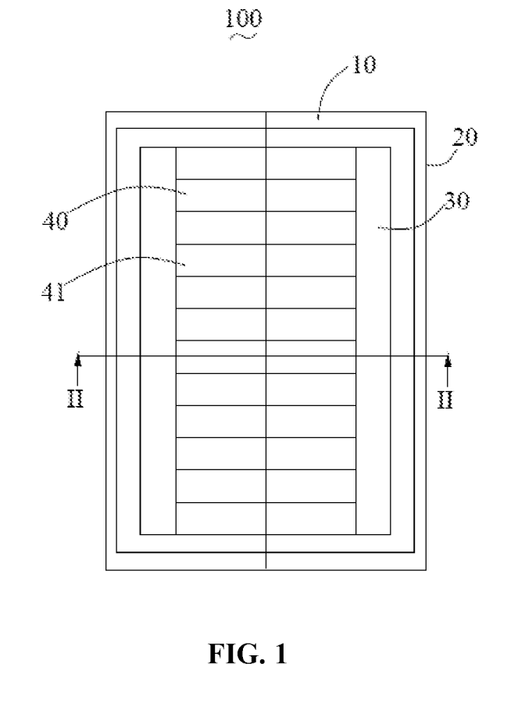
FIG. 1 is a top view of a 3D ultrasound imaging system in accordance with an embodiment of the present patent application.

FIG. 1 is a top view of a 3D ultrasound imaging system in accordance with an embodiment of the present patent application. Referring to FIG. 1, the 3D ultrasound imaging system 100 in accordance with an embodiment of the present patent application includes an outer housing 10, a circuit board 20, multiple transceiver chips 30 and multiple sensor modules 40.

Figure 2:
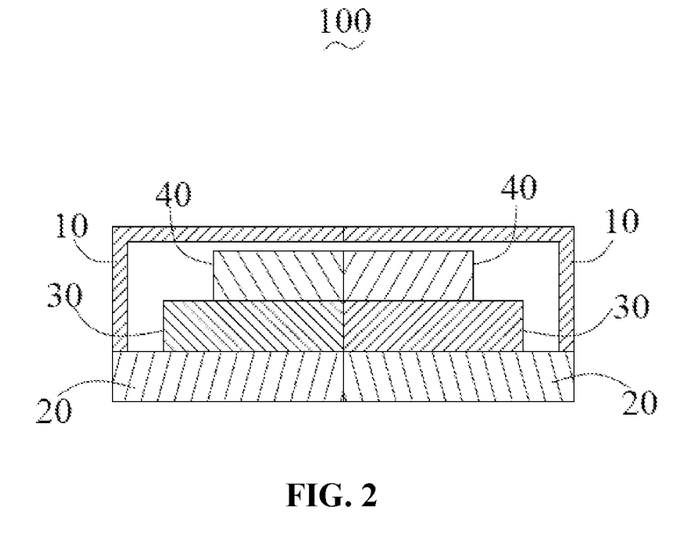
FIG. 2 is a cross-sectional view taken along the II-II line of the 3D ultrasound imaging system as depicted in FIG. 1.

Referring to FIG. 2, the outer housing 10 is made of conductive materials (e.g. aluminum) and capable of being connected to the ground so as to resist electromagnetic interference. In this embodiment, the outer housing 10 is covering over the circuit board 20 so that an accommodating cavity is formed and configured to accommodate the multiple transceiver chips 30 and the multiple sensor modules 40.

In this embodiment, the outer housing 10 is jointly formed by two symmetrical parts. In other embodiments, the outer housing 10 can be a unibody structure.

The multiple transceiver chips 30 are integrated on the circuit board 20 and jointed sequentially, thus forming a matrix structure. The circuit board 20 is configured to electrically connect each electronic component in the transceiver chip 30.

In this embodiment, the multiple transceiver chips 30 are formed into a matrix with 12 rows and 2 columns so as to reduce the size of the 3D ultrasound imaging system 100. Of course, the rows and columns of the matrix structure are not limited to the rows and columns in this embodiment and can be determined according to requirements. In other embodiments, the multiple transceiver chips 30 can also be jointed into a non-matrix according to requirements (e.g. shapes of the Chinese characters "十" and "米", etc.).

In this embodiment, the circuit board 20 is jointly formed by two symmetrical parts and each column of transceiver chips 30 are integrated on one of the two parts. In other embodiments, the circuit board 20 can be a unibody structure.

The multiple sensor modules 40 are integrated on the multiple transceiver chips 30 and individually corresponding to the multiple transceiver chips 30. Each sensor module 40 is integrated on a corresponding transceiver chip 30 and connected with the corresponding transceiver chip 30. The multiple sensor modules 40 are sequentially jointed and thus forming a matrix structure.

Figure 3:
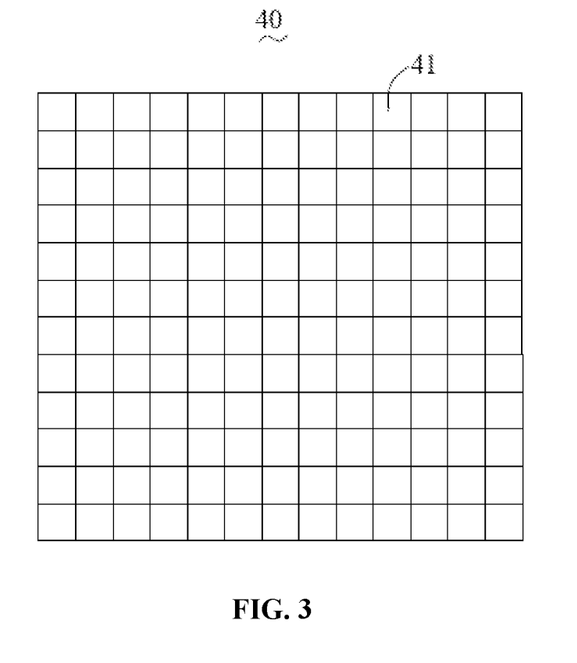
FIG. 3 illustrates the structure of a sensor module of the 3D ultrasound imaging system as depicted in FIG. 1.

Referring to FIG. 3, each sensor module 40 includes multiple sensor units 41. In this embodiment, the multiple sensor units 41 are sequentially jointed into a matrix structure so as to reduce the size of the 3D ultrasound imaging system 100. In this embodiment, each sensor unit 41 includes a piezoelectric sensor.

Figure 4:
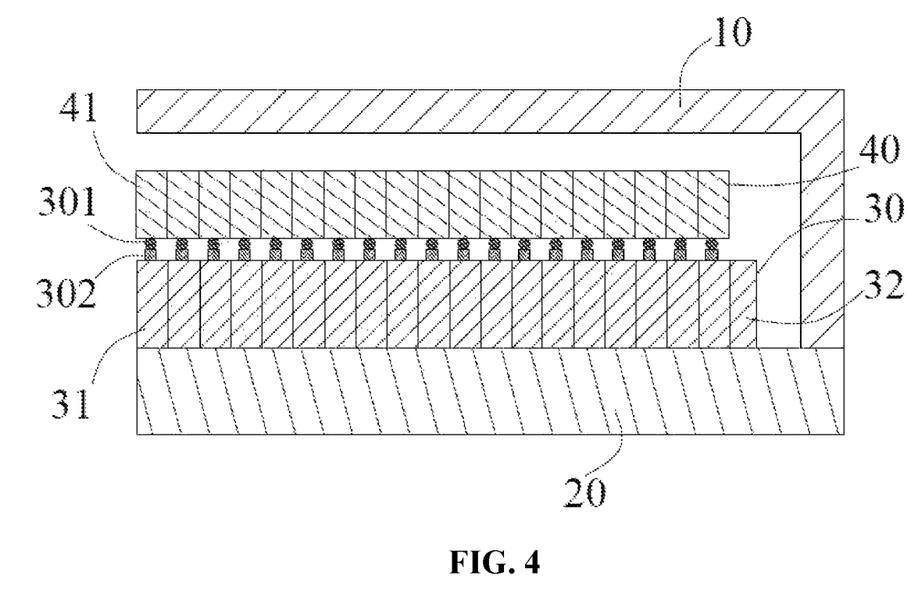
FIG. 4 illustrates the internal structure of half of the 3D ultrasound imaging system as depicted in FIG. 1.

Referring to FIG. 4, each transceiver chip 30 includes multiple unit circuits 31 in an arrangement of a matrix and multiple row sharing circuits 32.

The multiple unit circuits 31 are individually corresponding to the multiple sensor units 41 and each unit circuit 31 is connected with a corresponding sensor unit 41. In this embodiment, each unit circuit 31 is connected with a corresponding sensor unit 41 through a metal ball 301 and a metal pad 302.

Figure 5:
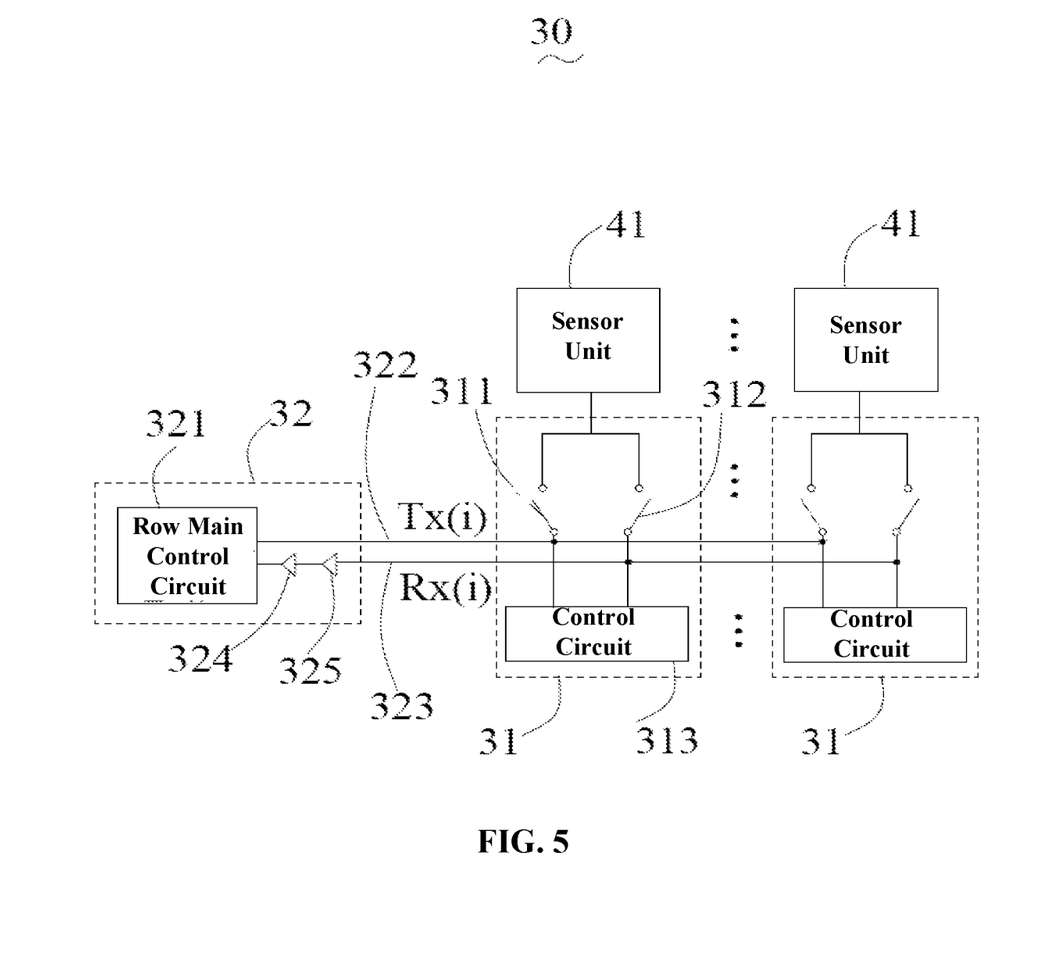
FIG. 5 illustrates a portion of the internal circuit of a transceiver chip of the 3D ultrasound imaging system as depicted in FIG. 1.

Referring to FIG. 5, each unit circuit 31 includes a first electrically controlled switch 311, a second electrically controlled switch 312 and a control circuit 313.

The first electrically controlled switch 311 is configured to control whether the corresponding sensor unit 41 participates transmission of ultrasound signals. The second electrically controlled switch 312 is configured to control whether the corresponding sensor unit 41 participates receiving of ultrasound signals. The control circuit 313 is configured to control the switching of the first electrically controlled switch 311 and the second electrically controlled switch 312. In this embodiment, the control circuit 313 is a programmable logic control circuit including a unit programmable memory. The unit programmable memory includes multiple shift registers and each shift register includes multiple flip-flops. The unit programmable memory is configured to fast select sensor units 41 which participate transmission or receiving of ultrasound signals.

Each row sharing circuit 32 is corresponding to a row of unit circuits 31 and configured to transmit control signals to the corresponding row of unit circuits 31.

The row sharing circuit 32 includes a row main control circuit 321, a signal transmission bus 322 and a signal receiving bus 323.

The signal transmission bus 322 and the signal receiving bus 323 extend through a corresponding row of unit circuits 31. The row main control circuit 321 of each row is configured to receive an external main control signal $\Phi x$, an external transmission control signal Tx-EN and an external receiving control signal Rx-EN (referring to FIG. 6) from a processor of the 3D ultrasound imaging system 100 and transmit the main control signal $\Phi x$, the transmission control signal Tx-EN and the receiving control signal Rx-EN to the multiple control circuits 313. Referring to FIG. 5, the unit circuits 31 which the signal transmission bus Tx (i) or the signal receiving bus Rx (i) extends through reside in the ith row of the matrix of the unit circuits.

Specifically, the first electrically controlled switch 311 is configured to control the conducting state between the corresponding sensor unit 41 and the signal transmission bus Tx(i), so as to control whether the corresponding sensor unit 41 participates transmission of ultrasound signals. The second electrically controlled switch 312 is configured to control the conducting state between the corresponding sensor unit 41 and the signal receiving bus Rx(i), so as to control whether the corresponding sensor unit 41 participates receiving of ultrasound signals.

In addition, each row sharing circuit 32 further includes a driver circuit 324 and a low-noise amplifier 325 which are sitting on the signal receiving bus Rx (i). The driver circuit 324 is connected with the multiple unit circuits 31 through the low-noise amplifier 325. The low-noise amplifier 325 is configured to amplify signals on the signal receiving bus Rx(i). The driver circuit 324 is configured to further amplify the output of the low-noise amplifier 325 and transmit the signals amplified by the driver circuit 324 to the row main control circuit 321.

Figure 6:
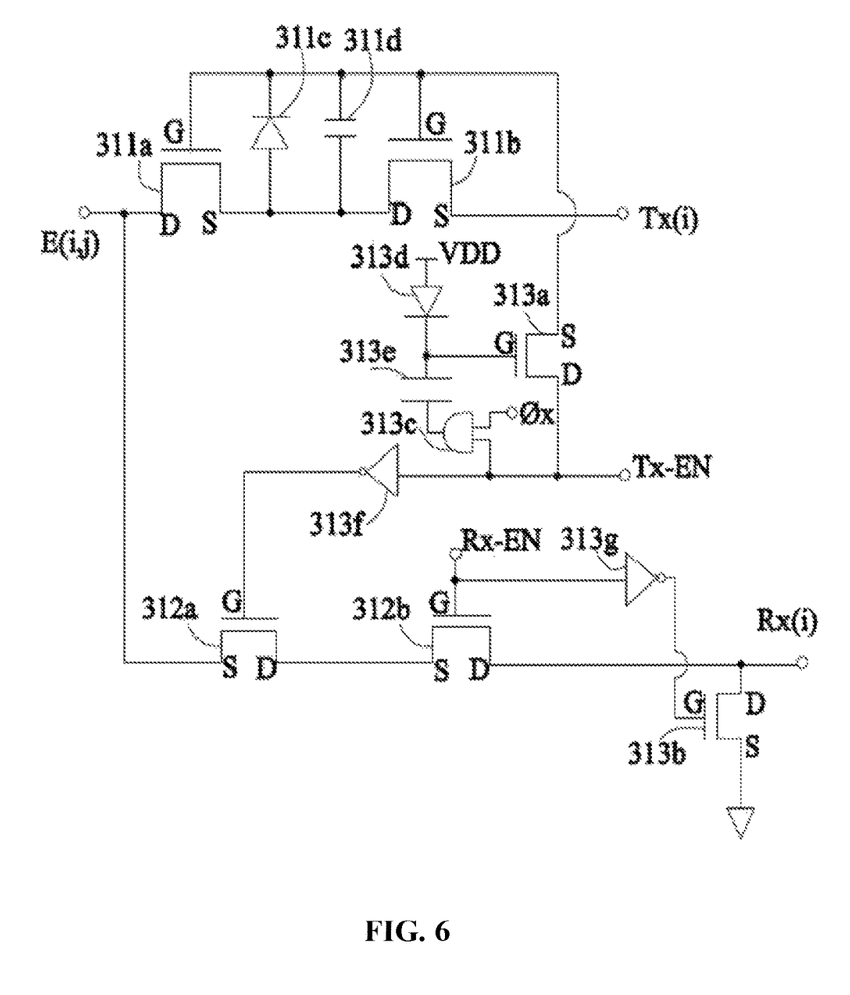
FIG. 6 is a schematic circuit diagram of a unit circuit of the 3D ultrasound imaging system as depicted in FIG. 1.

Referring to FIG. 6, in this embodiment, the first electrically controlled switch 311 includes a first electronic switch 311a, a second electronic switch 311b and a voltage regulator module. The second electrically controlled switch 312 includes a third electronic switch 312a and a fourth electronic switch 312b. The control circuit 313 includes a first main control electronic switch 313a, a second main control electronic switch 313b, an AND gate chip 313c, a diode 313d, a capacitor 313e, a first inverter 313f and a second inverter 313g.

The first electronic switch 311a, the second electronic switch 311b, the third electronic switch 312a, the fourth electronic switch 312b, the first main control electronic switch 313a and the second main control electronic switch 313b are N-type Metal-Oxide Semiconductor Field Effect Transistors, each including a gate electrode, a drain electrode and a source electrode.

The drain electrode of the first electronic switch 311a is connected with a corresponding sensor unit E (i, j) (i.e. the sensor unit disposed in the ith row and the jth column), the source electrode of the first electronic switch 311a is connected with the drain electrode of the second electronic switch 311b while the gate electrode of the first electronic switch 311a is connected with the gate electrode of the second electronic switch 311b. The source electrode of the second electronic switch 311b is connected with the signal transmission bus Tx (i).

The source electrode of the first main control electronic switch 313a is connected with the gate electrode of the first electronic switch 311a; the drain electrode of the first main control electronic switch 313a receives the transmission control signal Tx-EN; the gate electrode of the first main control electronic switch 313a is connected with a reference voltage VDD through the diode 313d; the positive electrode of the diode 313d is connected with the reference voltage VDD while the negative electrode of the diode 313d is connected with the gate electrode of the first main control electronic switch 313a. The gate electrode of the first main control electronic switch 313a is connected with the output port of the AND gate chip 313c through the capacitor 313e. A first input port of the AND gate chip 313c receives the main control signal Φx and a second input port of the AND gate chip 313c receives the transmission control signal Tx-EN.

The source electrode of the third electronic switch 312a is connected with the corresponding sensor unit E (i, j); the drain electrode of the third electronic switch 312a is connected with the source electrode of the fourth electronic switch 312b; the gate electrode of the third electronic switch 312a receives the transmission control signal Tx-EN through the first inverter 313f. The output port of the first inverter 313f is connected with the gate electrode of the third electronic switch 312a; the input port of the first inverter 313f receives the transmission control signal Tx-EN. The gate electrode of the fourth electronic switch 312b receives the receiving control signal Rx-EN; the drain electrode of the fourth electronic switch 312b is connected with the signal receiving bus Rx (i).

The drain electrode of the second main control electronic switch 313b is connected with the signal receiving bus Rx (i); the source electrode of the second main control electronic switch 313b is connected to the ground; the gate electrode of the second main control electronic switch 313b receives the receiving control signal Rx-EN through the second inverter 313g. The input port of the second inverter 313g receives the receiving control signal Rx-EN and the output port of the second inverter 313g is connected with the gate electrode of the second main control electronic switch 313b.

Further, the first electrically controlled switch 311 further includes the voltage regulator module configured to keep the voltage between the gate electrode and the source electrode of the first electronic switch 311a constant, so as to protect the first electronic switch 311a and prevent the first electronic switch 311a from breaking down because of an excessively high transient voltage between the gate electrode and the source electrode of the first electronic switch 311a. The voltage regulator module includes a voltage regulating diode 311c and a voltage regulating capacitor 311d. The positive electrode of the voltage regulating diode 311c is connected with the source electrode of the first electronic switch 311a; the negative electrode of the voltage regulating diode 311c is connected with the gate electrode of the first electronic switch 311a. The voltage regulating capacitor 311d is connected in parallel with the voltage regulating diode 311c.

The operating process of the unit circuit 31 is as follows: (1) When the sensor unit E (i, j) is selected to transmit ultrasound signals, the transmission control signal Tx-EN is set as a high level "1" and the main control signal Φx is set as a high level "1", and therefore the output port of the AND gate chip 313c outputs a high level "1". The voltage of the gate electrode of the first main control electronic switch 313a is increased to a value greater than the reference voltage VDD, so that the signal at the gate electrode of the first main control electronic switch 313a changes to a high level "1" and the drain electrode and the source electrode of the first main control electronic switch 313a are conducted. At this time, the gate electrode of the first electronic switch 311a and the gate electrode of the second electronic switch 311b receive the transmission control signal Tx-EN and signals at the gate electrodes of the first electronic switch 311a and the second electronic switch 311b change to a high level "1", and therefore the drain electrode of the first electronic switch 311a are conducted to the source electrode of the first electronic switch 311a while the drain electrode of the second electronic switch 311b are conducted to the source electrode of the second electronic switch 311b, so that the sensor unit E (i, j) is connected with the signal transmission bus Tx (i). Since the transmission control signal Tx-EN is a high level "1" at this moment, the output port of the first inverter 313f outputs a low level "0", so that the signal at the gate electrode of the third electronic switch 312a is a low level, the drain electrode and the source electrode of the third electronic switch 312a are disconnected while the sensor unit E (i, j) and the signal receiving bus Rx (i) are disconnected. As a result, the sensor unit E (i, j) cannot receive ultrasound signals at this moment. In other words, when the sensor unit E (i, j) transmits ultrasound signals, the sensor unit E (i, j) cannot receive ultrasound signals. And vice versa, when the sensor unit E (i, j) is selected to receive ultrasound signals, the receiving control signal Rx-EN is set as a high level "1" and the transmission control signal Tx-EN is set as a low level "0" and therefore cannot transmit ultrasound signals.

In addition, when the sensor unit E (i, j) is not selected to receive ultrasound signals but selected only to transmit ultrasound signals, the receiving control signal Rx-EN is set as a low level "0", so that the drain electrode and the source electrode of the fourth electronic switch 312b are disconnected. At this time, the second inverter 313g receives the receiving control signal Rx-EN and outputs a high level "1" while the signal at the gate electrode of the second main control electronic switch 313b changes to a high level "1", so that the drain electrode and the source electrode of the second main control electronic switch 313b are conducted. Therefore, the signal receiving bus Rx (i) is connected to the ground and signals of unselected sensor units E (i, j) are effectively prevented from coupling into the signal receiving bus Rx (i).

In this embodiment, the first electronic switch 311a and the second electronic switch 311b are High voltage Lateral Double-Diffused Metal-Oxide-Semiconductor field effect transistors. The peak voltage of the signal transmission bus Tx (i) is 30V. Since the first electrically controlled switch 311 in the present patent application includes two electronic switches (i.e. the first electronic switch 311a and the second electronic switch 311b), signal attenuation produced by capacitive load can be effectively reduced while the first electrically controlled switch 311 is not affected even if there is a short circuit between two adjacent sensor units 41 because of manufacturing defects. Compared with circuits consisting of latches, the circuit of the present patent application is more compact and therefore helps to save area and integrate.

In this embodiment, the structures of transceiver chips 30 in a same row are identical. In a transceiver chip 30, each row of unit circuits 31 share a same row sharing circuit 32, a same signal transmission bus Tx (i) and a same signal receiving bus Rx (i) and occupy a data channel, so that the number of data channel is not too big even if the sensor module 40 integrates in a large scale. For example, each row of unit circuits 31 in the transceiver chip 30 include n unit circuits 31 and the n unit circuits 31 share a row sharing circuit 32.

In other embodiments, the structures of transceiver chips 30 in a same row can be different and only one transceiver chip 30 in each row of transceiver chips 30 is required to have multiple row sharing circuits 32. The signal transmission buses Tx(i) and the signal receiving buses Rx(i) of the multiple row sharing circuits 32 extend through other transceiver chips 30 without row sharing circuits 32, so that other transceiver chips 30 can receive control signals from corresponding row sharing circuits 32. For example, if the number of transceiver chips 30 in a row of transceiver chips 30 is a while a row of unit circuits 31 in each transceiver chip 30 include n unit circuits 31, then a×n unit circuits 31 share one row sharing circuit 32.

The multiple row sharing circuits 32 can transmit control instructions so as to select corresponding sensor units 41 to transmit or receive ultrasound signals. Sensor units 41 selected to transmit or receive ultrasound signals are formed into a pattern.

It is understood that according to different requirements of medical imaging, users expect that the 3D ultrasound imaging system has different operating modes for users to select as required, and in other words, to realize reconfigurability of operating modes. Specifically, two schemes are taken as an example. Scheme A is selecting all sensor units 41 in a column at a time and then selecting a next adjacent column of sensor units 41. Suppose there are 10 columns of target sensor units 41, then ten images need to be transmitted 10 times and the 10 images are synthesized so that the image resolution of the synthesized image is high and the details are clear but it is relatively time-consuming (e.g. it takes 0.1 second to transmit image signals for one time and therefore it takes 1 second to produce a complete image) and the time resolution is relatively low. Scheme B is selecting all sensor units 41 at a time so that the image needs to be transmitted only once, which saves much time (it takes only 0.1 second to produce a complete image). However, the details of such an image, which is taken by one time, are less clear than the details of images produced by scheme A and the spatial resolution is relatively low, which has the effect of "exchanging spatial resolution for time resolution". In the practical operating process, if users have relatively high requirements for spatial resolution, scheme A is adopted; if users have relatively high requirements for time resolution, scheme B is adopted.

Of course, in the practical operating process, if users only need to acquire images of some particular locations, the usage position and direction of the multiple sensor modules 40 need to be configured, and therefore some sensor units 41 must be selected as target sensor units for operating while other sensor units 41 do not operate. The multiple row sharing circuits 32 have the following three operating modes.

Figure 7A:
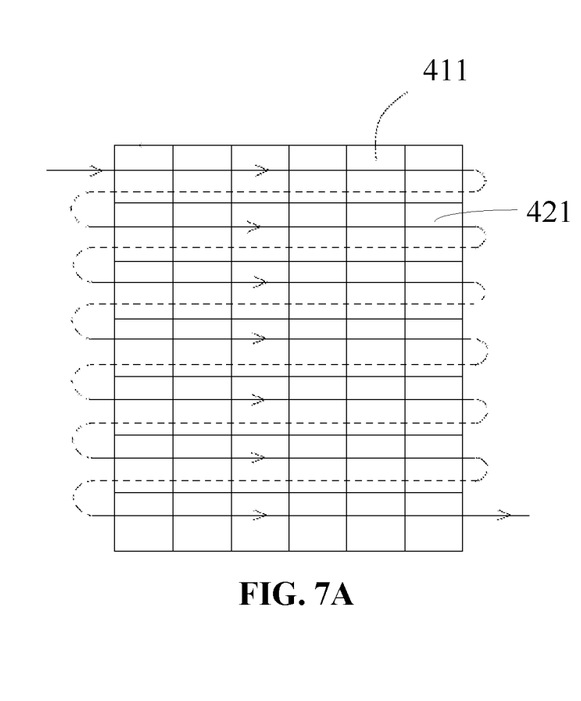
FIG. 7A illustrates the first selection mode of selecting sensor units of the 3D ultrasound imaging system as depicted in FIG. 1.

The first operating mode: referring to FIG. 4 and FIG. 7A, the multiple row sharing circuits 32 operate sequentially; after the row sharing circuit 32 of the first row selects a target sensor unit 411 from the corresponding row (i.e. the first row) of sensor units 41, the row sharing circuit 32 of the second row begins to select a target sensor unit 421 from the corresponding row of sensor units 41. The process goes on until all row sharing circuits 32 finish selecting the target sensor units for the corresponding rows.

Figure 7B:
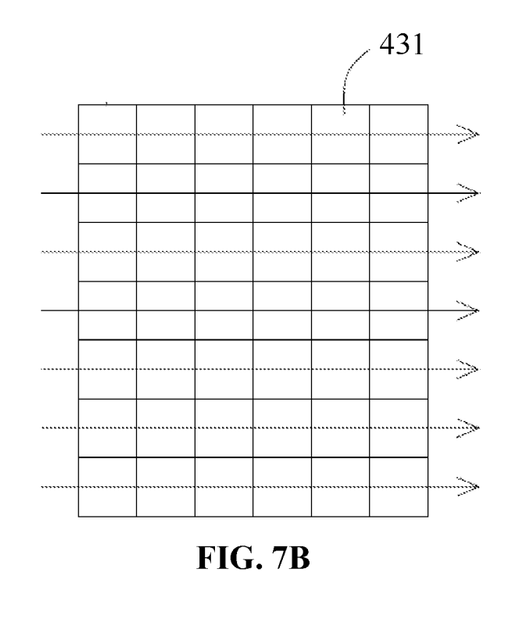
FIG. 7B illustrates the second operating mode of selecting sensor units of the 3D ultrasound imaging system as depicted in FIG. 1.

The second operating mode: referring to FIG. 7B, the multiple row sharing circuits 32 operate simultaneously and select sensor units in a predetermined column (e.g. the Pth column) from the sensor units 41 in all corresponding rows as the target sensor units 431.

Figure 7C:
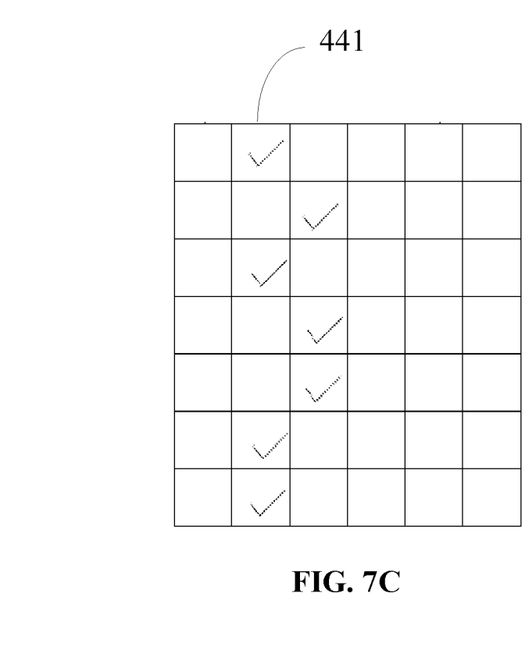
FIG. 7C and FIG. 7D illustrate the third operating mode of selecting sensor units of the 3D ultrasound imaging system as depicted in FIG. 1.
Figure 7D:
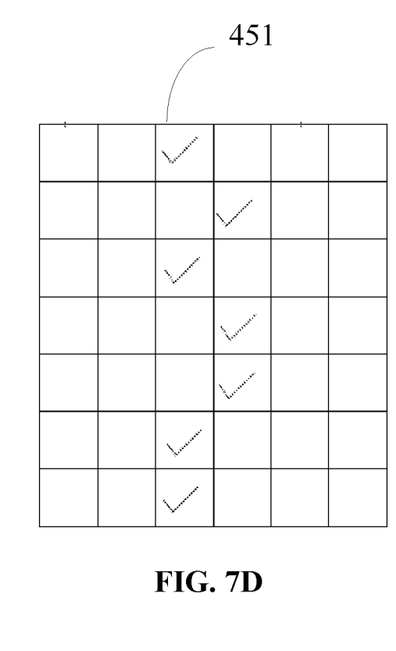

The third operating mode: referring to FIG. 7C, the multiple row sharing circuits 32 operate simultaneously and each row sharing circuit 32 first selects a sensor unit 41 from the corresponding row of sensor units 41 as a preset sensor unit 441; then referring to FIG. 7D, the multiple row sharing circuits 32 operate simultaneously and each row sharing circuit 32 selects a sensor unit 41 adjacent to the preset sensor unit by one or multiple columns from the corresponding row of sensor units 41 as the target sensor unit 451.

Users can select a required operating mode according to practical medical requirements of ultrasound detection, which effectively realizes the reconfigurability of operating modes, greatly reduces the time period for selecting sensor units 41 and effectively improves the operating efficiency.

Compared with conventional 3D ultrasound imaging systems, the 3D ultrasound imaging system of the present patent application forms a large sensor matrix through jointing multiple sensor modules, and is applicable to systems with large scale integrated sensors. At the same time, since at least one of transceiver chips in a same row has multiple row sharing circuits, each row of unit circuits share a row sharing circuit, so that the number of data channel is not too big even if the large scale sensor modules are integrated. Besides, row sharing circuits have avoided repeating configuring some circuits (e.g. low-noise amplifier) in each unit circuit, so that the unit circuits are more compact, which helps to improve the density of integration. In addition, diverse and fast selection of required sensor units can be realized by configuring a unit programmable memory in the control circuit of each unit circuit, so that the usage position and direction of the multiple sensor modules have stronger reconfigurability and can be fast switchable from multiple specific and complex configuration schemes and therefore the operating efficiency is effectively improved.

While the present patent application has been shown and described with particular references to a number of embodiments thereof, it should be noted that various other changes or modifications may be made without departing from the scope of the present invention.

What is claimed is:

1. A 3D ultrasound imaging system comprising:
    a plurality of sensor units;
    a plurality of unit circuits corresponding to the plurality of sensor units and connected with the plurality of sensor units respectively, each unit circuit comprising a first electrically controlled switch, a second electrically controlled switch and a control circuit; and
    a plurality of row sharing circuits, each row sharing circuit comprising a signal transmission bus, a signal receiving bus and a row main control circuit, each row of unit circuits sharing a row sharing circuit; wherein:
    the signal transmission bus and the signal receiving bus of each row sharing circuit extend through a corresponding row of unit circuits;
    the row main control circuit of each row is configured to transmit main control signals, transmission control signals and receiving control signals to a corresponding row of unit circuits so as to select the corresponding sensor units to transmit or receive ultrasound signals;

the first electrically controlled switch is configured to control whether the corresponding sensor unit participates transmission of ultrasound signals;

the second electrically controlled switch is configured to control whether the corresponding sensor unit participates receiving of ultrasound signals;

the control circuit is a programmable logic control circuit configured to control switching of the first electrically controlled switch and the second electrically controlled switch;

the first electrically controlled switch comprises a first electronic switch and a second electronic switch;

the second electrically controlled switch comprises a third electronic switch and a fourth electronic switch;

the control circuit comprises a first main control electronic switch, a second main control electronic switch, an AND gate chip, a diode, a capacitor, a first inverter and a second inverter;

the first electronic switch, the second electronic switch, the third electronic switch, the fourth electronic switch, the first main control electronic switch and the second main control electronic switch are N-type Metal-Oxide Semiconductor Field Effect Transistors, each comprising a gate electrode, a drain electrode and a source electrode;

the drain electrode of the first electronic switch is connected with a corresponding sensor unit, the source electrode of the first electronic switch is connected with the drain electrode of the second electronic switch and the gate electrode of the first electronic switch is connected with the gate electrode of the second electronic switch;

the source electrode of the second electronic switch is connected with the signal transmission bus;

the source electrode of the first main control electronic switch is connected with the gate electrode of the first electronic switch, the drain electrode of the first main control electronic switch receives the transmission control signal and the gate electrode of the first main control electronic switch is connected with a reference voltage through the diode;

the gate electrode of the first main control electronic switch is connected with the output port of the AND gate chip through the capacitor;

a first input port of the AND gate chip receives the main control signal and a second input port of the AND gate chip receives the transmission control signal;

the source electrode of the third electronic switch is connected with the corresponding sensor unit, the drain electrode of the third electronic switch is connected with the source electrode of the fourth electronic switch and the gate electrode of the third electronic switch receives the transmission control signal through the first inverter;

the gate electrode of the fourth electronic switch receives the receiving control signal and the drain electrode of the fourth electronic switch is connected with the signal receiving bus; and the drain electrode of the second main control electronic switch is connected with the signal receiving bus, the source electrode of the second main control electronic switch is connected to the ground and the gate electrode of the second main control electronic switch receives the receiving control signal through the second inverter.

2. The 3D ultrasound imaging system of claim 1 further comprising a circuit board, a plurality of transceiver chips and a plurality of sensor modules, wherein the plurality of transceiver chips are integrated on the circuit board and jointed sequentially, and thus forming a matrix structure; the plurality of sensor modules are jointed sequentially and thus forming a matrix structure and individually corresponding to the plurality of transceiver chips; each sensor module is integrated on a corresponding transceiver chip respectively; each sensor module comprises the plurality of sensor units in an arrangement of a matrix; each transceiver chip comprises the plurality of unit circuits in an arrangement of a matrix; at least one transceiver chip of each row of transceiver chips comprises the plurality of row sharing circuits.

3. A 3D ultrasound imaging system comprising:
a circuit board;
a plurality of transceiver chips; and
a plurality of sensor modules; wherein:
the plurality of transceiver chips are integrated on the circuit board;
the plurality of sensor modules are individually corresponding to the plurality of transceiver chips;
each sensor module is integrated on a corresponding transceiver chip respectively;
each sensor module comprises a plurality of sensor units;
each transceiver chip comprises a plurality of unit circuits;
the plurality of unit circuits are individually corresponding to the plurality of sensor units and connected with the plurality of sensor units respectively;
at least one transceiver chip of each row of transceiver chips comprises a plurality of row sharing circuits;
each row of unit circuits share a row sharing circuit;
the row sharing circuit comprises a signal transmission bus, a signal receiving bus and a row main control circuit;
the signal transmission bus and the signal receiving bus of each row sharing circuit extend through a corresponding row of unit circuits;
the row main control circuit of each row is configured to transmit main control signals, transmission control signals and receiving control signals to a corresponding row of unit circuits so as to select the corresponding sensor units to transmit or receive ultrasound signals;
each unit circuit comprises a first electrically controlled switch, a second electrically controlled switch and a control circuit;
the first electrically controlled switch is configured to control whether the corresponding sensor unit participates transmission of ultrasound signals;
the second electrically controlled switch is configured to control whether the corresponding sensor unit participates receiving of ultrasound signals;
the control circuit is configured to control switching of the first electrically controlled switch and the second electrically controlled switch;
the first electrically controlled switch comprises a first electronic switch and a second electronic switch;
the second electrically controlled switch comprises a third electronic switch and a fourth electronic switch;
the control circuit comprises a first main control electronic switch, a second main control electronic switch, an AND gate chip, a diode, a capacitor, a first inverter and a second inverter;
the first electronic switch, the second electronic switch, the third electronic switch, the fourth electronic switch, the first main control electronic switch and the second main control electronic switch are N-type Metal-Oxide Semiconductor Field Effect Transistors, each comprising a gate electrode, a drain electrode and a source electrode;

the drain electrode of the first electronic switch is connected with the corresponding sensor unit, the source electrode of the first electronic switch is connected with the drain electrode of the second electronic switch and the gate electrode of the first electronic switch is connected with the gate electrode of the second electronic switch;

the source electrode of the second electronic switch is connected with the signal transmission bus;

the source electrode of the first main control electronic switch is connected with the gate electrode of the first electronic switch, the drain electrode of the first main control electronic switch receives the transmission control signal and the gate electrode of the first main control electronic switch is connected with a reference voltage through the diode;

the gate electrode of the first main control electronic switch is connected with the output port of the AND gate chip through the capacitor;

a first input port of the AND gate chip receives the main control signal and a second input port receives the transmission control signal;

the source electrode of the third electronic switch is connected with the corresponding sensor unit, the drain electrode of the third electronic switch is connected with the source electrode of the fourth electronic switch and the gate electrode of the third electronic switch receives the transmission control signal through the first inverter;

the gate electrode of the fourth electronic switch receives the receiving control signal and the drain electrode of the fourth electronic switch is connected with the signal receiving bus; and the drain electrode of the second main control electronic switch is connected with the signal receiving bus, the source electrode of the second main control electronic switch is connected to the ground and the gate electrode of the second main control electronic switch receives the receiving control signal through the second inverter.

4. The 3D ultrasound imaging system of claim 3, wherein the plurality of transceiver chips are jointed sequentially and thus forming a matrix structure; the plurality of sensor modules are jointed sequentially and thus forming a matrix structure.

5. The 3D ultrasound imaging system of claim 3, wherein each transceiver chip in a row of transceiver chips comprises the plurality of row sharing circuits and each row sharing circuit only transmits main control signals, transmission control signals and receiving control signals to the corresponding row of unit circuits in the transceiver chip.

6. The 3D ultrasound imaging system of claim 3, wherein only one transceiver chip in a row of transceiver chips comprises the plurality of row sharing circuits and each row sharing circuit transmits main control signals, transmission control signals and receiving control signals to the corresponding row of unit circuits in all transceiver chips.

7. The 3D ultrasound imaging system of claim 3, wherein each row sharing circuit further comprises a driver circuit and a low-noise amplifier which are sitting on the signal receiving bus; the driver circuit is connected with the plurality of unit circuits through the low-noise amplifier; the low-noise amplifier is configured to amplify signals on the signal receiving bus; the driver circuit is configured to further amplify the output of the low-noise amplifier and transmit the signals amplified by the driver circuit to the row main control circuit.

8. The 3D ultrasound imaging system of claim 3, wherein the plurality of row sharing circuits operate sequentially; after the row sharing circuit of the first row selects a target sensor unit from the corresponding row of sensor units, the row sharing circuit of the second row begins to select a target sensor unit from the corresponding row of sensor units; the process goes on until all row sharing circuits finish selecting the target sensor units for the corresponding rows.

9. The 3D ultrasound imaging system of claim 3, wherein the plurality of row sharing circuits operate simultaneously and select sensor units in a predetermined column from the sensor units in all corresponding rows as the target sensor units.

10. The 3D ultrasound imaging system of claim 3, wherein the plurality of row sharing circuits operate simultaneously and each row sharing circuit first selects a sensor unit from the corresponding row of sensor units as a preset sensor unit; then the plurality of row sharing circuits operate simultaneously and each row sharing circuit selects a sensor unit adjacent to the preset sensor unit by one or a plurality of columns from the corresponding row of sensor units as the target sensor unit.

11. A 3D ultrasound imaging system comprising:
a plurality of sensor units;
a plurality of unit circuits corresponding to the plurality of sensor units and connected with the plurality of sensor units respectively, each unit circuit comprising a first electrically controlled switch, a second electrically controlled switch and a control circuit; and
a plurality of row sharing circuits, each row sharing circuit comprising a signal transmission bus, a signal receiving bus and a row main control circuit, each row of unit circuits sharing a row sharing circuit; wherein:
the signal transmission bus and the signal receiving bus of each row sharing circuit extend through a corresponding row of unit circuits;
the row main control circuit of each row is configured to transmit main control signals, transmission control signals and receiving control signals to a corresponding row of unit circuits so as to select the corresponding sensor units to transmit or receive ultrasound signals;
the first electrically controlled switch is configured to control whether the corresponding sensor unit participates transmission of ultrasound signals;
the second electrically controlled switch is configured to control whether the corresponding sensor unit participates receiving of ultrasound signals;
the control circuit is a programmable logic control circuit configured to control switching of the first electrically controlled switch and the second electrically controlled switch;
the first electrically controlled switch comprises a first electronic switch and a second electronic switch;
the second electrically controlled switch comprises a third electronic switch and a fourth electronic switch; and
the control circuit comprises a first main control electronic switch, a second main control electronic switch, an AND gate chip, a diode, a capacitor, a first inverter and a second inverter.

12. The 3D ultrasound imaging system of claim 11, wherein the first electronic switch, the second electronic switch, the third electronic switch, the fourth electronic switch, the first main control electronic switch and the second main control electronic switch are N-type Metal- Oxide Semiconductor Field Effect Transistors, each comprising a gate electrode, a drain electrode and a source electrode.

13. The 3D ultrasound imaging system of claim 12, wherein the drain electrode of the first electronic switch is connected with a corresponding sensor unit, the source electrode of the first electronic switch is connected with the drain electrode of the second electronic switch and the gate electrode of the first electronic switch is connected with the gate electrode of the second electronic switch.

14. The 3D ultrasound imaging system of claim 13, wherein the source electrode of the second electronic switch is connected with the signal transmission bus; the source electrode of the first main control electronic switch is connected with the gate electrode of the first electronic switch, the drain electrode of the first main control electronic switch receives the transmission control signal and the gate electrode of the first main control electronic switch is connected with a reference voltage through the diode.

15. The 3D ultrasound imaging system of claim 14, wherein the gate electrode of the first main control electronic switch is connected with the output port of the AND gate chip through the capacitor; a first input port of the AND gate chip receives the main control signal and a second input port of the AND gate chip receives the transmission control signal.

16. The 3D ultrasound imaging system of claim 14, wherein the source electrode of the third electronic switch is connected with the corresponding sensor unit, the drain electrode of the third electronic switch is connected with the source electrode of the fourth electronic switch and the gate electrode of the third electronic switch receives the transmission control signal through the first inverter; the gate electrode of the fourth electronic switch receives the receiving control signal and the drain electrode of the fourth electronic switch is connected with the signal receiving bus; and the drain electrode of the second main control electronic switch is connected with the signal receiving bus, the source electrode of the second main control electronic switch is connected to the ground and the gate electrode of the second main control electronic switch receives the receiving control signal through the second inverter.

17. The 3D ultrasound imaging system of claim 16 further comprising a circuit board; a plurality of transceiver chips; and a plurality of sensor modules.

18. The 3D ultrasound imaging system of claim 17, wherein the plurality of transceiver chips are integrated on the circuit board and jointed sequentially, and thus forming a matrix structure; the plurality of sensor modules are jointed sequentially and thus forming a matrix structure and individually corresponding to the plurality of transceiver chips.

19. The 3D ultrasound imaging system of claim 18, wherein each sensor module is integrated on a corresponding transceiver chip respectively; each sensor module comprises the plurality of sensor units in an arrangement of a matrix; each transceiver chip comprises the plurality of unit circuits in an arrangement of a matrix.

20. The 3D ultrasound imaging system of claim 19, wherein at least one transceiver chip of each row of transceiver chips comprises the plurality of row sharing circuits.

* * * * *